United States Patent
Zappala

(10) Patent No.: US 6,773,428 B2
(45) Date of Patent: Aug. 10, 2004

(54) IMPLANTABLE DELIVERY SYSTEM AND METHOD FOR THE PHARMACOLOGIC MANAGEMENT OF ERECTILE DYSFUNCTION

(76) Inventor: Stephen M. Zappala, 98 Rattlesnake Hill Rd., Andover, MA (US) 01810

( * ) Notice: Subject to any disclaimer, the term of this patent is extended or adjusted under 35 U.S.C. 154(b) by 3 days.

(21) Appl. No.: 09/853,223

(22) Filed: May 11, 2001

(65) Prior Publication Data

US 2001/0041824 A1 Nov. 15, 2001

Related U.S. Application Data

(60) Provisional application No. 60/204,066, filed on May 12, 2000.

(51) Int. Cl.$^7$ ................................................ A61K 9/22
(52) U.S. Cl. ........................................................ 604/890.1
(58) Field of Search ............................... 604/891.1, 264, 604/265, 272, 502, 890.1, 19, 48, 93.01, 131, 132, 151, 523, 537, 288.01–288.04; 600/40, 38–39

(56) References Cited

U.S. PATENT DOCUMENTS

| | | | | |
|---|---|---|---|---|
| 3,386,438 A | * | 6/1968 | Stevens | 604/272 |
| 4,544,371 A | * | 10/1985 | Dormandy et al. | 604/891.1 |
| 4,559,931 A | * | 12/1985 | Fischell | 600/40 |
| 4,574,792 A | * | 3/1986 | Trick | 600/40 |
| 4,588,394 A | * | 5/1986 | Schulte et al. | 604/9 |
| 4,769,016 A | * | 9/1988 | Labianca | 604/266 |
| 4,828,544 A | * | 5/1989 | Lane et al. | 604/9 |
| 4,838,887 A | * | 6/1989 | Idriss | 604/891.1 |
| 5,135,516 A | * | 8/1992 | Sahatjian et al. | 604/265 |
| 5,237,993 A | * | 8/1993 | Skrabal | 600/309 |
| 5,575,770 A | * | 11/1996 | Melsky et al. | 604/288.04 |
| 5,578,006 A | * | 11/1996 | Schon | 604/264 |
| 5,830,172 A | * | 11/1998 | Leveen et al. | 604/8 |
| 5,925,629 A | * | 7/1999 | Place | 514/179 |
| 5,931,829 A | * | 8/1999 | Burbank et al. | 604/502 |
| 6,033,398 A | * | 3/2000 | Farley et al. | 604/113 |
| 6,102,884 A | * | 8/2000 | Squitieri | 604/8 |
| 6,132,405 A | * | 10/2000 | Nilsson et al. | 604/264 |
| 6,132,415 A | * | 10/2000 | Finch et al. | 604/502 |
| 6,245,039 B1 | * | 6/2001 | Brugger et al. | 604/29 |
| 6,364,855 B1 | * | 4/2002 | Zappala | 604/96.01 |
| 6,585,681 B2 | * | 7/2003 | Brugger et al. | 604/29 |

* cited by examiner

Primary Examiner—Loan H. Thanh
(74) Attorney, Agent, or Firm—Jenifer E. Haeckl, Esq.; Mirick, O'Connell, DeMallie & Lougee, LLP

(57) ABSTRACT

An implantable delivery system of the invention for managing a patient's erectile dysfunction, generally comprises: one or more reservoir members adapted to be substantially implanted in the patient's scrotal pouch and to at least temporarily store one or more pharmacologic agents; one or more diaphragms for accessing and refilling one or more of the reservoir members with one or more of the pharmacologic agents; one or more distal end members comprising one or more perforations for dispensing at least a portion of the pharmacologic agents into one or both of the patient's cavernosal bodies; one or more conduits for transporting at least a portion of the pharmacologic agents from the reservoir member to the distal end member; and one or more pumps for causing at least a portion of the pharmacologic agents to be transported from the reservoir member to the distal end member.

10 Claims, 2 Drawing Sheets

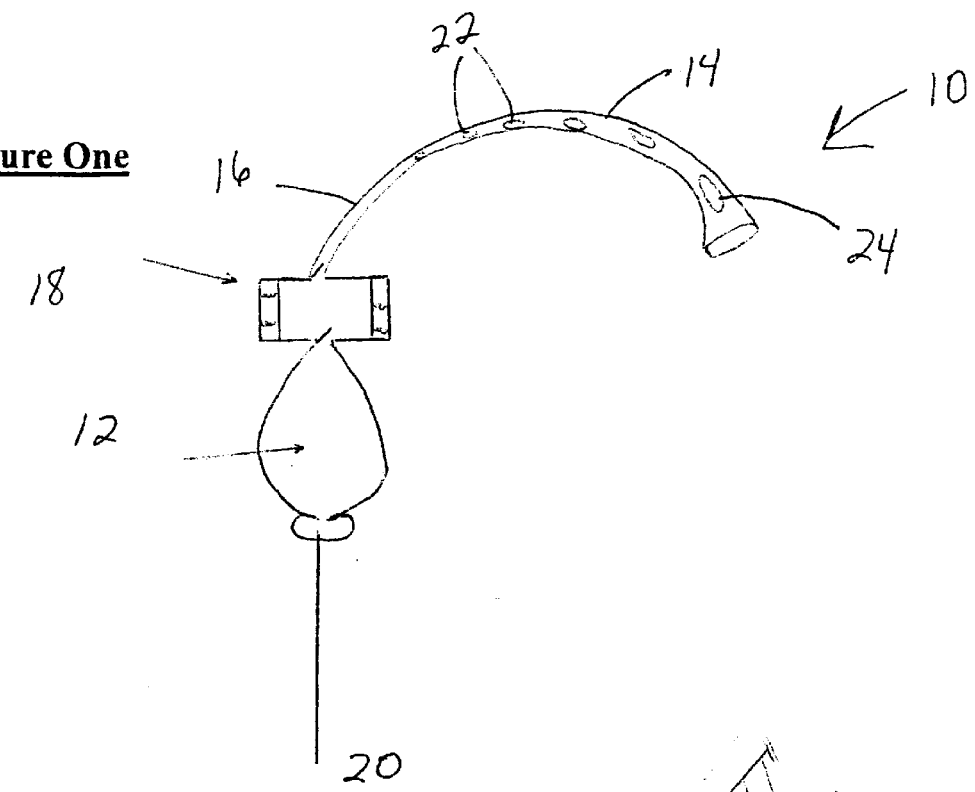
Figure One
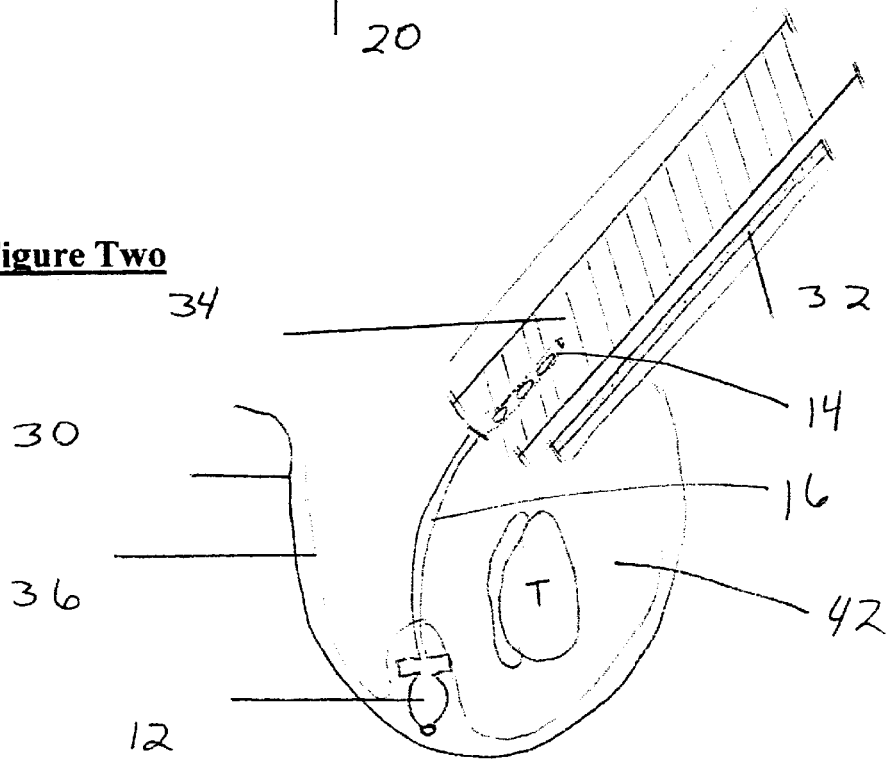
Figure Two

Figure Three
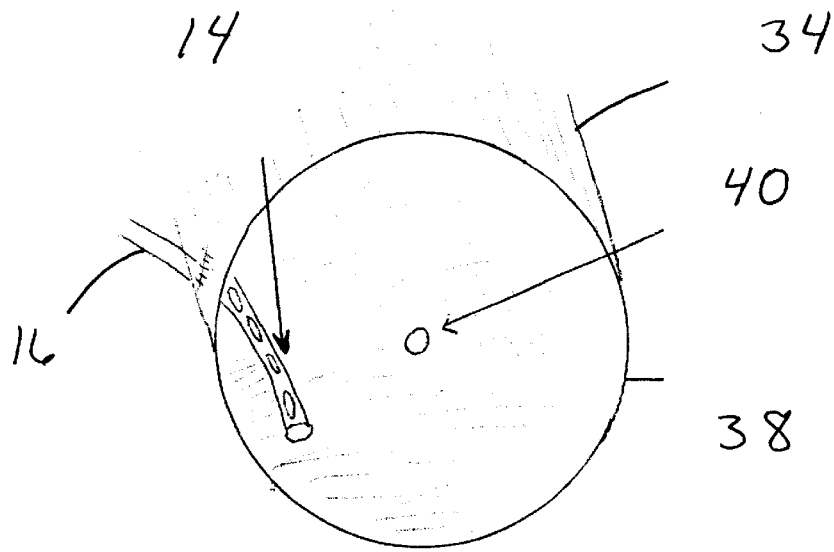
Figure Four
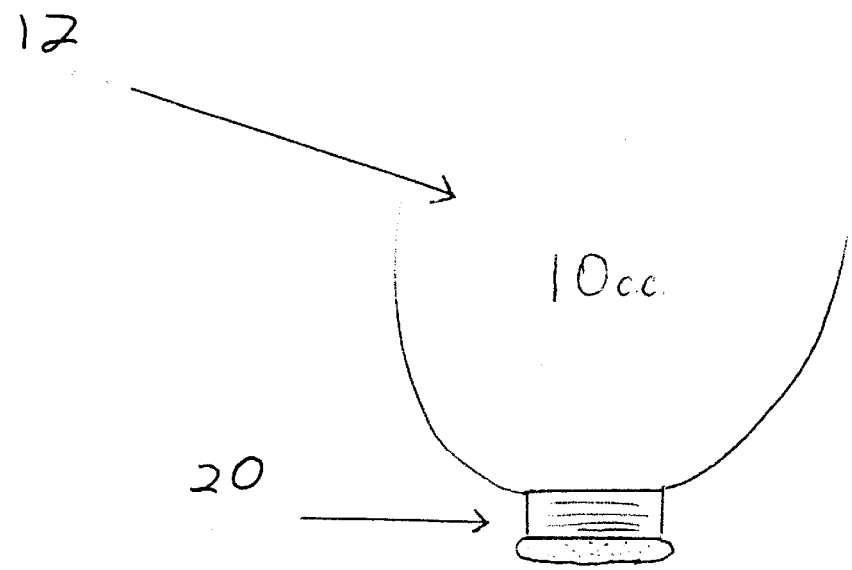

IMPLANTABLE DELIVERY SYSTEM AND METHOD FOR THE PHARMACOLOGIC MANAGEMENT OF ERECTILE DYSFUNCTION

This application claims the benefit of Provisional application No. 60/204,066 filed May 12, 2000.

FIELD OF THE INVENTION

The invention relates to devices for managing erectile dysfunction and more specifically to an implantable device for delivering pharmacologic agents into the cavernosal body.

BACKGROUND OF THE INVENTION

Erectile dysfunction, which is the persistent inability to attain and maintain penile erection sufficient for intercourse, is a major health issue among males and especially among the aging male population. The causes of erectile dysfunction include vasculogenic, neurogenic, endocrinilogic and psychogenic causes. Management options for erectile dysfunction depend on the cause of the dysfunction and include medical and surgical therapies and vacuum erection devices, each with their own limitations and complications.

Medical therapies include the oral, transcutaneous (penile injection) and transurethral (e.g. MUSE System) routes of delivery of various pharmacologic agents. See, for example, U.S. Pat. No. 5,916,569 to Spencer et al., U.S. Pat. No. 5,925,629 to Place, and U.S. Pat. No. 6,156,753 to Doherty, Jr. et al. However, many men are not suitable candidates for oral agents such as sildenafil (Viagra; Pfizer, New York), a phosphodiesterase inhibitor, because of potential life threatening interactions with cardiac medications such as nitrates.

Penile (intracavernosal) injection therapy with vasodilator agents such as prostaglandin $E_1$, papaverine, nitric oxide, phentolamine, apomorphine, or pharmacologic intestinal peptide (VIP) is a well-accepted method. The technique however must be taught to anxious patients with careful attention to the dose injection sites, and the amount of the agent. Many patients withdraw from intracavernosal injection therapy because of the anxiety associated with self-injection, recurrent cutaneous ecchymoses, painful injections, or associated corporal fibrosis (Peyronie's Disease). Moreover, patients are uncomfortable when they travel through public airports or to foreign countries with syringes and medications. These limitations, associated with the complete loss of spontaneity, are the main reasons for discontinuation in an otherwise successful pharmacologic erection program.

Surgically invasive procedures have been reserved for those men who fail conservative therapies; these options include revascularization procedures, penile prostheses and cavernous nerve stimulation devices, e.g. U.S. Pat. No. 5,938,584 to Ardito et al. and U.S. Pat. No. 6,169,924 B1 to Meloy et al. Penile prostheses are generally last resort because implantation results in irreparable damage to the nerves and musculature.

SUMMARY OF THE INVENTION

It is therefore a primary object of this invention to provide a system and method for managing erectile dysfinction that is effective, does not cause irreparable damage to the nerves and musculature, and allows for spontaneity.

It is a further object of this invention to provide a system for managing erectile dysfunction with pharmacologic agents that is implantable and refillable.

The preferred embodiment of the implantable delivery system of the invention for managing a patient's erectile dysfunction, generally comprises: one or more reservoir members adapted to be substantially implanted in the patient's scrotal pouch and to at least temporarily store one or more pharmacologic agents; one or more means for accessing and refilling one or more of the reservoir members with one or more of the pharmacologic agents; one or more distal end members comprising one or more means for dispensing at least a portion of the pharmacologic agents into one or both of the patient's cavernosal bodies; one or more means for transporting at least a portion of the pharmacologic agents from the reservoir member to the distal end member; and one or more means for causing at least a portion of the pharmacologic agents to be transported from the reservoir member to the distal end member. At least one of the means for accessing and refilling preferably comprises a self-sealing diaphragm that is capable of being punctured with a needle and is integral with the reservoir member and at least one of the means for dispensing preferably comprises one or more distal catheter members provided with one or more perforations through which one or more of the pharmacologic agents are capable of passing.

One or more of the distal catheter members may comprise a plurality of graduated perforations, from a proximal portion of the distal catheter member to a distal portion of the distal catheter member, that are adapted to facilitate distribution of the pharmacologic agents evenly within the cavernosal body; wherein one or more of the distal catheter members may further comprise an increasingly graduated inner diameter, from a proximal portion of the distal catheter member to a distal portion of the distal catheter member, that is adapted to facilitate distribution of the pharmacologic agents evenly within the cavernosal body.

The means for transporting preferably comprises one or more heparin-coated, sialastic catheters and the means for causing the agents to be transported preferably comprises, one or more pressure-sensitive valves and at least one pump member that interacts with the reservoir member to release a predetermined dose of the pharmacologic agents from the reservoir member to the means for transporting.

Another preferred embodiment of the implantable delivery system of the invention for managing a patient's erectile dysfunction, comprises: one or more reservoir members adapted to be substantially implanted in the patient's scrotal pouch and to at least temporarily store one or more pharmacologic agents; one or more means for accessing and refilling one or more of the reservoir members with one or more of the pharmacologic agents; one or more distal end members comprising one or more perforations for dispensing at least a portion of the pharmacologic agents into one or both of the patient's cavernosal bodies; one or more conduits for transporting at least a portion of the pharmacologic agents from the reservoir member to the distal end member; and one or more pumps that interact with one or more of the reservoir members to release a predetermined dose of at least a portion of the pharmacologic agents from the reservoir member into one or more of the conduits. One or more of the means for accessing and filling may comprise one or more self-sealing diaphragms.

The preferred method of the invention, for managing a patient's erectile dysfunction, generally comprises the steps of: providing an implantable delivery device, comprising, one or more reservoir members that is provided with a self-sealing diaphragm and adapted to be substantially implanted in the patient's scrotal pouch and to at least temporarily store one or more pharmacologic agents, one or more distal end members comprising one or more perforations for dispensing at least a portion of the pharmacologic agents into one or both of the patient's cavernosal bodies, one or more conduits for transporting at least a portion of the pharmacologic agents from the reservoir member to the distal end member, and one or more pumps that interact with one or more of the reservoir members to release an effective amount of at least a portion of the pharmacologic agents from the reservoir member into one or more of the conduits; surgically implanting the device so that, at least one of the reservoirs is implanted in the patient's subdartos scrotal pouch so that the diaphragm can be accessed with a needle; and at least one of the distal end members is implanted subtunically in at least one of the patient's corpus cavernosal bodies; filling at least one of the reservoirs with one or more of the pharmacologic agents by puncturing the diaphragm with a needle containing the pharmacologic agents and injecting the pharmacologic agents into the reservoirs; activating the pump to release the pharmacologic agents into the conduit to allow the released pharmacologic agents to be transported and dispensed into at least one of the cavernosal bodies; and refilling the reservoir with the pharmacologic agents as needed.

BRIEF DESCRIPTION OF THE DRAWINGS

Other objects, features and advantages will occur to those skilled in the art from the following description of the preferred embodiments and the accompanying drawings in which:

FIG. 1 is a side view of the preferred embodiment of the device of the invention;

FIG. 2 is a cross-sectional side view of the preferred embodiment shown in FIG. 1 implanted according to the method of the invention;

FIG. 3 is an enlarged perspective view of the distal portion of the device of the invention implanted subtunically in the cavenosal body shown in cross-section; and FIG. 4 is an enlarged partial side view of the reservoir and diaphragm of the device of the invention.

DETAILED DESCRIPTION OF THE PREFERRED EMBODIMENTS AND METHODS

The inventive implantable device for managing erectile dysfunction features a subcutaneous refillable resevoir, which is attached to a metered pump mechanism as a delivery vehicle for pharmacologic agents including, but not limited to, vasoactive agents. The device is preferably a one-piece apparatus connected to the cavernosal body through a six French heparin coated, sialastic, perforated catheter. A self-sealing diaphragm is located at the dependent portion of the device. The diaphragm may be punctured using sterile techniques by a urologist with a twenty-five gauge needle to fill the resevoir with the pharmacologic agent that the physician chooses. The catheter is positioned in a sub-tunical location using a Seldinger Technique to prevent disturbing or altering the central vasculature of the corpus cavernosum. The catheter should have limited thrombogenicity and create a minimal pseudocapsule.

FIG. 1 is an enlarged schematic side view of the entire device (not drawn to scale). FIG. 2 shows the device implanted in the surgical position, with the resevoir/pump in the sub-dartos scrotal pouch, and the perforated catheter within one of the cavernosal bodies. The preferred embodiment of the device of the invention is shown in FIG. 1 and is generally referred to as device 10. Device 10 is designed to be implanted within the individual's body as shown in FIGS. 2 and 4 and to be refilled as needed by puncturing the diaphragm of the reservoir of the device (FIG. 4) through the scrotal skin 30 with a needle and injecting the pharmacologic agent into the reservoir of the device.

Device 10 generally includes one or more reservoir members 12 adapted to be substantially implanted under the dartos 36 in the patient's scrotal pouch 42 and to at least temporarily store one or more pharmacologic agents (not shown); one or more self-sealing diaphragms 20 for accessing and refilling one or more of the reservoir members 12 with one or more of the pharmacologic agents; one or more distal end members 14 comprising one or more perforations (e.g. 22, 24) for dispensing at least a portion of the pharmacologic agents into one or both of the patient's cavernosal bodies 34 located within and along the length of the urethra 32; one or more conduits 16 for transporting at least a portion of the pharmacologic agents from the reservoir member 12 to the distal end member 14; and one or more pumps 18 for causing at least a portion of the pharmacologic agents to be transported from the reservoir member to the distal end member. Pump 18 and/or conduits 16 preferably include a series of pressure sensitive valves. The pump and/or pressure sensitive valves minimize overdosages and unwanted rapid instillation of medication. Distal end member 14 is implanted under the tunica albuginea in the cavernosal body using the Seldinger Technique to prevent damage or alterations to the central vasculature and cavernosal artery 40 of the cavernosal body.

The perforations or openings should be large enough to allow the pharmacologic agents to pass from the catheter into the cavernosal body. The inner diameter of distal end member 14 and the individual perforations should increase is size towards the distal end of the catheter to cause the agents released from the reservoir to flow readily to and out of the end of the distal end member. The increase in size facilitates even distribution of the agent within the cavenosal cavity. The size and type of perforations or openings will depend on the material used for the catheter and distal end member, the pharmacologic agents and on the internal pressure of the catheter created by the pump and pressure sensitive valves in the system.

The preferred method of the invention for managing erectile dysfunction begins with the step of providing the implantable delivery device 10 of the invention, comprising, one or more reservoir members 12 that is provided with a self-sealing diaphragm 20 and adapted to be substantially implanted in the patient's scrotal pouch and to at least temporarily store one or more pharmacologic agents, one or more distal end members 14 comprising one or more perforations for dispensing at least a portion of the pharmacologic agents into one or both of the patient's cavernosal bodies, one or more conduits for transporting at least a portion of the pharmacologic agents from the reservoir member to the distal end member, and one or more pumps that interact with one or more of the reservoir members to release an effective amount of at least a portion of the pharmacologic agents from the reservoir member into one or more of the conduits; surgically implanting the device so that, at least one of the reservoirs is implanted in the patient's subdartos scrotal pouch so that the diaphragm can be accessed with a needle; and at least one of the distal end members is implanted subtunically in at least one of the patient's corpus cavernosal bodies; filling at least one of the reservoirs with one or more of the pharmacologic agents by puncturing the diaphragm with a needle containing the pharmacologic agents and injecting the pharmacologic agents into the reservoirs; activating the pump to release the pharmacologic agents into the conduit to allow the released pharmacologic agents to be transported and dispensed into at least one of the cavernosal bodies; and refilling the reservoir with the pharmacologic agents as needed.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. An implantable delivery system for managing a patient's erectile dysfunction, comprising,
    at least one reservoir members adapted to be substantially implanted in the patient's scrotal pouch and to at least temporarily store one or more pharmacologic agents;
    at least one means for accessing and refilling one or more of said reservoir members with one or more of said pharmacologic agents;
    at least one distal end members comprising at least one means for dispensing at least a portion of said pharmacologic agents into one or both of the patient's cavernmosal bodies;
    at least one means for transporting at least a portion of said pharmacologic agents from said reservoir member to said distal end member; and
    at least one means for causing at least a portion of said pharmacologic agents to be transported from said reservoir member to said distal end member;
wherein said distal catheter member comprises a plurality of graduated perforations, from a proximal portion of said distal catheter member to a distal portion of said distal catheter member, that are adapted to facilitate distribution of said pharmacologic agents evenly within the cavernmosal body.

2. The device of claim 1, wherein said means for causing said agents to be transported comprises, at least one pressure-sensitive valve and at least one pump member that interacts with said reservoir member to release a predetermined dose of said pharmacologic agents from said reservoir member to said means for transporting.

3. The device of claim 1, wherein said means for accessing and filling comprises one or more self-sealing diaphragms.

4. The device of claim 1, wherein said means for causing at least a portion of said pharmacologic agents to be transported from said reservoir member to said distal end member comprises a series of pressure sensitive valves.

5. The device of claim 1, wherein said means for causing at least a portion of said pharmacologic agents to be transported from said reservoir member to said distal end member comprises a series of pressure sensitive valves.

6. The device of claim 1, wherein one or more of said pharmacologic agents is selected from a group consisting of prostaglandin $E_1$, papaverine, nitric oxide, phentolamine, apomorphine, and pharmacologic intestinal peptide.

7. An implantable delivery system for managing a patient's erectile dysfunction, comprising,
    at least one reservoir members adapted to be substantially implanted in the patient's scrotal pouch and to at least temporarily store one or more pharmacologic agents;
    at least one means for accessing and refilling one or more of said reservoir members with one or more of said pharmacologic agents;
    at least one distal end member comprising at least one means for dispensing at least a portion of said pharmacologic agents into one or both of the patient's cavernosal bodies;
    at least one means for transporting at least a portion of said pharmacologic agents from said reservoir member to said distal end member; and
    at least one means for causing at least a portion of said pharmacologic agents to be transported from said reservoir member to said distal end member;
wherein said distal catheter member has an increasingly graduated inner diameter, from a proximal portion of said distal catheter member to a distal portion of said distal catheter member, that is adapted to facilitate distribution of said pharmacologic agents evenly within the cavernmosal body.

8. An implantable delivery system for managing a patient's erectile dysfunction, comprising,
    at least one reservoir member adapted to be substantially implanted in the patient's scrotal pouch and to at least temporarily store one or more pharmacologic agents;
    at least one means for accessing and refilling one or more of said reservoir members with one or more of said pharmacologic agents;
    at least one distal end member comprising at least one means for dispensing at least a portion of said pharmacologic agents into one or both of the patient's cavernosal bodies;
    at least one means for transporting at least a portion of said pharmacologic agents from said reservoir member to said distal end member; and
    at least one means for causing at least a portion of said pharmacologic agents to be transported from said reservoir member to said distal end member;
wherein at least one of said distal end members comprises, a series of perforations that increase in size from a proximal portion of said distal end member to a distal portion of said distal end member, and wherein said distal end members has an increasingly graduated inner diameter from a proximal portion of said distal end member to a distal portion of said distal end member.

9. An implantable delivery system for managing a patient's erectile dysfunction, comprising,
    at least one reservoir members adapted to be substantially implanted in the patient's scrotal pouch and to at least temporarily store one or more pharmacologic agents;
    at least one means for accessing and refilling said reservoir member with one or more of said pharmacologic agents; at least one distal end members comprising one or more perforations for dispensing at least a portion of said pharmacologic agents into one or both of the patient's cavernosal bodies;
    at least one conduits for transporting at least a portion of said pharmacologic agents from said reservoir member to said distal end member; and
    at least one pump that interact with said reservoir members to release a predetermined dose of at least a portion of said pharmacologic agents from said reservoir member into said conduits;
wherein at least one of said distal end members comprises, a series of perforations that increase in size from a proximal portion of said distal end member to a distal portion of said distal end member, and wherein at least one of said distal end members has an increasingly graduated inner diameter from a proximal portion of said distal end member to a distal portion of said distal end member.

10. The device of claim 1, wherein one or more of said pharmacologic agents is a vasodilator.

* * * * *